US005876980A

United States Patent [19]
DeFrees et al.

[11] Patent Number: 5,876,980
[45] Date of Patent: *Mar. 2, 1999

[54] ENZYMATIC SYNTHESIS OF OLIGOSACCHARIDES

[75] Inventors: Shawn DeFrees, San Marcos; Robert J. Bayer, San Diego; Murray Ratcliffe, Carlsbad, all of Calif.

[73] Assignee: Cytel Corporation, San Diego, Calif.

[*] Notice: The term of this patent shall not extend beyond the expiration date of Pat. No. 5,728,554.

[21] Appl. No.: 419,659

[22] Filed: Apr. 11, 1995

[51] Int. Cl.$^6$ ............................ C12P 19/18; C12P 19/12; C12P 19/04; C12P 19/00
[52] U.S. Cl. ................................ 435/97; 435/72; 435/74; 435/84; 435/100; 435/101
[58] Field of Search ................................ 435/97, 72, 74, 435/84, 100, 101

[56] References Cited

U.S. PATENT DOCUMENTS

| | | | |
|---|---|---|---|
| 5,164,374 | 11/1992 | Rademacher et al. | 514/23 |
| 5,278,299 | 1/1994 | Wong et al. | 536/53 |
| 5,288,637 | 2/1994 | Roth | 435/288 |
| 5,352,670 | 10/1994 | Venot | 514/54 |

FOREIGN PATENT DOCUMENTS

| | | |
|---|---|---|
| WO 92/16640 | 10/1992 | WIPO . |
| WO 94/26760 | 11/1994 | WIPO . |
| WO 9425615 A | 11/1994 | WIPO . |

OTHER PUBLICATIONS

Carlson et al, J. Biol. Chem. 248(16):5742–5750 (1973).
DeLuca, et al. (1995) *J. Am. Chem. Soc.* 117:5869–5870.
Ito, et al. (1993) *Pure Appl. Chem.* 65:753.
Van den Eijnden, et al. (1981) *J. Biol. Chem.*, 256:3159.
Weinstein, et al. (1982) *J. Biol. Chem.*, 257:13845.
Wen et al. (1992) *J. Biol. Chem.*, 267:21011.
Rearick, et al. (1979) *J. Biol. Chem.*, 254:4444.
Gillespie, et al. (1992) *J. Biol. Chem.*, 267:21004.
Kurosawa, et al. (1994) *Eur. J. Biochem.*, 219:375–381.
Gross, et al. (1987) *Eur. J. Biochem.*, 168:595.
Vijay, et al. (1975) *J. Biol. Chem.*, 250(1):164.
Zapata, et al. (1989) *J. Biol. Chem.*, 264(25):14769.
Higa, et al. (1985) *J. Biol. Chem.*, 260(15):8838.
Vann, et al. (1987) *J. Biol. Chem.*, 262:17556.
Shames, et al. (1991) *Glycobiology*, 1:187.
Ichikawa, et al. (1991) *J. Am. Chem. Soc.*, 113:4698–4700.
David, et al. (1987) "Immobilized enzymes in preparative carbohydrate chemistry", *Pure & Applied Chem.*, 59(11):1501–1508.
Auge, et al. (1990) *Carbohydrate Research* 200:257–268.
Auge, et al. (1986) *Carbohydrate Research* 151:147–156.

*Primary Examiner*—Francisco Prats
*Attorney, Agent, or Firm*—Townsend and Townsend and Crew

[57] ABSTRACT

The present invention provides improved methods for the preparation of sialyl galactosides. The methods use sialyl transferase cycle in which the reaction conditions are optimized to provide increased yields.

20 Claims, 1 Drawing Sheet

ENZYMATIC SYNTHESIS OF OLIGOSACCHARIDES

CROSS-REFERENCE TO RELATED APPLICATIONS

This application is related to copending application, Ser. No. 08/419,669, filed Apr. 11, 1995.

FIELD OF THE INVENTION

The present invention relates to the synthesis of oligosaccharides. In particular, it relates to improved enzymatic syntheses of such compounds in a single vessel using readily available starting materials.

BACKGROUND OF THE INVENTION

Increased understanding of the role of carbohydrates as recognition elements on the surface of cells has led to increased interest in the production of carbohydrate molecules of defined structure. For instance, compounds comprising the oligosaccharide moiety, sialyl lactose, have been of interest as neutralizers for enterotoxins from bacteria such as *Vibrio cholerae, Eschericia coli,* and Salmonella (see, e.g., U.S. Pat. No. 5,330,975). Sialyl lactose has also been investigated for the treatment of arthritis and related autoimmune diseases. In particular, sialyl lactose is thought to inhibit or disrupt the degree of occupancy of the Fc carbohydrate binding site on IgG, and thus prevent the formation of immune complexes (see, U.S. Pat. No. 5,164,374). Recently, sialyl$\alpha$(2,3)galactosides, sialyl lactose and sialyl lactosamine have been proposed for the treatment of ulcers, and Phase I clinical trials have begun for the use of the former compound in this capacity. See, Balkonen, et al, *FEMS Immunology and Medical Microbiology* 7:29 (1993) and BioWorld Today, p. 5, Apr. 4, 1995. In addition, sialyl lactose is useful as food supplement, for instance in baby formula.

Because of interest in making desired carbohydrate structures, glycosyltransferases and their role in enzyme-catalyzed synthesis of carbohydrates are presently being extensively studied. These enzymes exhibit high specificity and are useful in forming carbohydrate structures of defined sequence. Consequently, glycosyltransferases are increasingly used as enzymatic catalysts in synthesis of a number of carbohydrates used for therapeutic and other purposes.

In the application of enzymes to the field of synthetic carbohydrate chemistry, the use of sialyltransferases for enzymatic sialylation offers advantages over chemical methods due to the virtually complete stereoselectivity and linkage specificity offered by the enzymes (Ito et al., *Pure Appl. Chem.,* 65:753 (1993) U.S. Pat. Nos. 5,352,670, and 5,374,541).

Improved methods for enzymatic synthesis of sialylated carbohydrate compounds would advance the production of a number of beneficial compounds. The present invention fulfills these and other needs.

SUMMARY OF THE INVENTION

The present invention provides improved methods for the preparation of sialyl galactosides. In particular, the methods comprise
 (a) providing a reaction medium comprising:
  (i) a sialyltransferase;
  (ii) a catalytic amount of a CMP-sialic acid synthetase;
  (iii) a sialic acid;
  (iv) an acceptor for said sialyltransferase having a galactosyl unit;
  (v) a CMP-sialic acid recycling system comprising at least 2 moles of phosphate donor per each mole of sialic acid, and catalytic amounts of an adenine nucleotide, a kinase capable of transferring phosphate from the phosphate donor to nucleoside diphosphates, and a nucleoside monophosphate kinase capable of transferring the terminal phosphate from a nucleoside triphosphate to CMP; and
  (vi) a divalent metal cation; and
 (b) maintaining a concentration of said divalent metal cation in said reaction medium of between about 2 mM and about 75 mM.

The divalent metal cation used in the methods can be $Mn^{++}$, $Mg^{++}$, $Ca^{++}$, $Co^{++}$, $Zn^{++}$ or combinations thereof. Typically the cation is $Mn^{++}$. The sialyltransferase is typically $\alpha$(2,3)sialyltransferase or $\alpha$(2,6)sialyltransferase. Preferred sialic acids include 5-N-acetylneuraminic acid. For the production of sialyl lactose, the acceptor is lactose.

The invention also provides sialyl lactose preparations of very high purity. These products are particularly useful in various therapeutic and diagnostic applications.

DETAILED DESCRIPTION OF THE INVENTION

Figure 1:
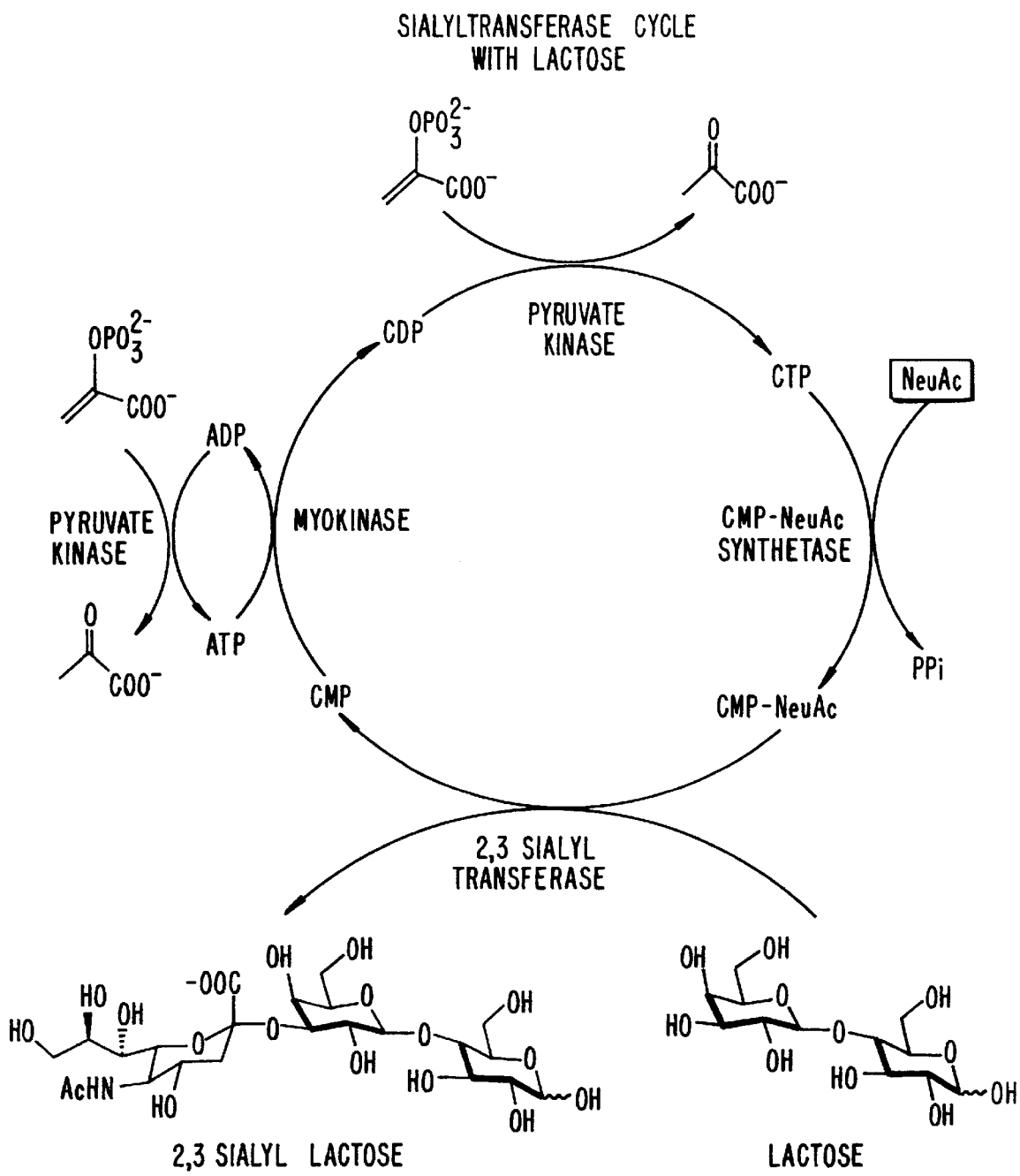
FIG. 1 illustrates a Sialyl Transferase cycle of the invention.

The present invention provides methods for production of sialyl oligosaccharides useful in various diagnostic and therapeutic applications. The methods rely on the use of sialyl transferase to catalyze the addition of a sialic acid residue to a substrate comprising a galactosyl residue at the non-reducing end of an oligosaccharide or carbohydrate moiety on a biomolecule. Thus, the products of the methods of the invention are referred to here as sialyl galactosides. Biomolecules as defined here include but are not limited to biologically significant molecules such as proteins (e.g., glycoproteins), and lipids (e.g., glycolipids, phospholipids, sphingolipids and gangliosides). Thus, the substrate for the sialyl transferases used in the methods of the invention can be any molecule comprising a galactosyl residue that can be sialylated by these enzymes. As explained below, a preferred substrate is lactose which is used to produce sialyl lactose.

The following abbreviations are used herein:
 Ara=arabinosyl;
 Fru=fructosyl;
 Fuc=fucosyl;
 Gal=galactosyl;
 GalNAc=N-acetylgalacto;
 Glc=glucosyl;
 GlcNAc=N-acetylgluco;
 Man=mannosyl; and
 NeuAc=sialyl (N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (i.e., Gal), followed by the configuration of the glycosidic bond ($\alpha$ or $\beta$), the ring bond (1 or 2), the ring position of the reducing saccharide involved in the bond (2, 3, 4, 6 or 8), and then the name or abbreviation of the reducing saccharide (i.e., GlcNAc). Each saccharide is a pyranose.

Embodiments of the Invention

A number of glycosyl transferase cycles (for example, the sialyltransferase cycles depicted in FIG. 1) are useful for the preparation of oligosaccharides. See, U.S. Pat. No. 5,374, 541 and WO 9425615 A. These enzyme cycles produce one mole of inorganic pyrophosphate for each mole of product formed and are typically carried out in the presence of a divalent metal ion. The metal ion is a cofactor for at least one of the enzymes in each of the cycles. However, the combination of pyrophosphate and some divalent metal cations produces a complex of particularly low solubility. This, in turn, results in reduced amounts of metal ions present in solution and a corresponding decrease in the overall turnover rates for those enzymes which require the metal ion cofactors. One potential solution to this problem involves beginning with large concentrations of metal ion cofactors. However, the use of large concentrations of metal ion cofactors has proven detrimental to both the galactosyltransferase and sialyltransferase cycles. Alternatively, others have incorporated inorganic pyrophosphatase into the reaction medium in an attempt to drive the reaction cycles to completion by removal of pyrophosphate. Nevertheless, complexes of limited solubility are formed between the orthophosphate produced by inorganic pyrophosphatase and the metal ion cofactor, with the effective reduction in metal ion concentrations.

Thus, the present invention provides in one aspect a method for increasing the yield in a sialyl transferase catalyzed formation of a glycosidic linkage. In this method a medium (typically an aqueous solution) containing a divalent metal cation is provided, and the concentration of the divalent metal cation in the reaction medium is maintained between about 2 mM and about 75 mM, preferably between about 5 mM and about 50 mM and more preferably between about 10 and about 40 mM.

By periodically monitoring the metal ion concentration in the reaction medium and supplementing the medium by additional amounts of divalent metal ions, the reaction cycles can be driven to completion within a suitable timeframe. Additionally, if more than one glycosyltransferase is used, consecutive cycles can be carried out in the same reaction vessel without isolation of the intermediate product. Moreover, by removing the inhibitory pyrophosphate, the reaction cycles can be run at substantially higher substrate (acceptor) concentration. Preferred divalent metal ions for use in the present invention include $Mn^{++}$, $Mg^{++}$, $Co^{++}$, $Ca^{++}$, $Zn^{++}$ and combinations thereof. More preferably, the divalent metal ion is $Mn^{++}$.

In one group of preferred embodiments, an aqueous medium contains, in addition to the sialyltransferase and a divalent metal cation, (i) a catalytic amount of a CMP-sialic acid synthetase, (ii) a sialic acid, (iii) an oligosaccharide acceptor for the sialyltransferase having a galactosyl unit at the oligosaccharide non-reducing terminus, and (iv) a CMP-sialic acid recycling system comprising at least 2 moles of phosphate donor per each mole of sialic acid, and catalytic amounts of a nucleoside triphosphate, a kinase capable of transferring phosphate from the phosphate donor to nucleoside diphosphates, and a nucleoside monophosphate kinase capable of transferring the terminal phosphate from a nucleoside triphosphate to CMP.

An α(2,3)sialyltransferase, often referred to as the sialyltransferase, is the principal enzyme utilized herein in the production of sialyl lactose. This enzyme transfers sialic acid (NeuAc) to a Gal with the formation of an α-linkage between the two saccharides. Bonding (linkage) between the saccharides is between the 2-position of NeuAc and the 3-position of Gal.

An exemplary α(2,3)sialyltransferase referred to as α(2, 3)sialtransferase (EC 2.4.99.6) transfers sialic acid to the non-reducing terminal Gal of a Galβ1→3Glc disaccharide or glycoside. See, Van den Eijnden et al., *J. Biol. Chem.*, 256:3159 (1981), Weinstein et al., *J. Biol. Chem.*, 257:13845 (1982) and Wen et al, *J. Biol. Chem.*, 267:21011 (1992). Another exemplary α-2,3-sialyltransferase (EC 2.4.99.4) transfers sialic acid to the non-reducing terminal Gal of the disaccharide or glycoside. See, Rearick et al., *J. Biol. Chem.*, 254:4444 (1979) and Gillespie et al., *J. Biol. Chem.*, 267:21004 (1992). Further exemplary enzymes include Galβ1,4-GlcNAc α-2,6 sialyltransferase (See, Kurosawa et al. *Eur. J. Biochem.* 219: 375–381 (1994)).

A second principle enzyme used in the present methods is CMP-sialic acid synthetase. This enzyme is utilized in the CMP-sialic acid regenerating system, discussed in detail hereinafter. CMP-sialic acid synthetase can be isolated and purified from cells and tissues containing the synthetase enzyme by procedures well known in the art. See, for example, Gross et al., *Eur. J. Biochem.*, 168:595 (1987), Vijay et al., *J. Biol. Chem.*, 250(1):164 (1975), Zapata et al., *J. Biol. Chem.*, 264(25):14769 (1989) and Higa et al., *J. Biol. Chem.*, 260(15):8838 (1985). The gene for this enzyme has also been sequenced. See, Vann et al., *J. Biol. Chem.*, 262:17556 (1987). An overexpression of the gene, has also been reported for use in a gram scale synthesis of CMP-NeuAc. See, Shames et al., *Glycobiology*, 1:187 (1991). This enzyme is also commercially available.

A sialic acid is also required. A contemplated sialic acid includes not only sialic acid itself (5-N-acetylneuraminic acid; 5-N-acetylamino-3,5-dideoxy-D-glycero-D-galacto-2-nonulosonic acid; NeuAc, and sometimes also abbreviated AcNeu or NANA), but also 9-substituted sialic acids such as a 9-O-$C_1$–$C_6$ acyl-NeuAc like 9-O-lactyl-NeuAc or 9-O-acetyl-NeuAc, 9-deoxy-9-fluoro-NeuAc and 9-azido-9-deoxy-NeuAc. The synthesis and use of these compounds in a sialylation procedure is disclosed in international application WO 92/16640, published Oct. 1, 1992.

The reaction mixture will also contain an acceptor for the sialyltransferase having a galactosyl unit. Suitable acceptors, include, for example, Galβ1→3GalNAc, lacto-N-tetraose, Galβ→3GlcNAc, Galβ1→3Ara, Galβ→6GlcNAc, Galβ1→4Glc (lactose), Galβ1→4Glcβ1-OCH$_2$CH$_3$, Galβ1→4Glcβ1-OCH$_2$CH$_2$CH$_3$, Galβ1→4Glcβ1-OCH$_2$C$_6$H$_5$, Galβ1→4GlcNAc, Galβ1-OCH$_3$, melibiose, raffinose, stachyose and lacto-N-neotetraose.

The CMP-sialic acid recycling system utilizes CMP-sialic acid synthetase as noted previously. As shown in FIG. 1, CMP-sialic acid (shown in FIG. 1 as CMP-NeuAc) reacts with a sialyltransferase acceptor in the presence of a α(2, 3)sialyltransferase to form the sialyl lactose.

The CMP-sialic acid regenerating system used in the present invention comprises cytidine monophosphate (CMP), a nucleoside triphosphate (for example adenosine triphosphate (ATP), a phosphate donor (for example, phosphoenolpyruvate or acetyl phosphate), a kinase (for example, pyruvate kinase or acetyl kinase) capable of transferring phosphate from the phosphate donor to nucleoside diphosphates and a nucleoside monophosphate kinase (for example, myolinase) capable of transferring the terminal phosphate from a nucleoside triphosphate to CMP. The previously discussed α(2,3)sialyltransferase and CMP-sialic acid synthetase can also be formally viewed as part of the CMP-sialic acid regenerating system. However, because those two enzymes have already been discussed, they will not be discussed further here.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system of the present invention are used to catalyze the phosphorylation of CMP. NMK's are commercially available (Sigma Chem. Co., St. Louis, Mo.; Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated acceptor saccharide. Preferred phosphate donors are phosphoenolpyruvate (PEP) and acetyl phosphate. A particularly preferred phosphate donor is PEP.

The selection of a particular kinase for use in accordance with the present invention depends upon the phosphate donor employed. When acetyl phosphate is used as the phosphate donor, the kinase is acetyl kinase. When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the stoichiometric substrates (free NeuAc or PEP) or acceptor is consumed.

Thus, in the sialylation example, CMP is converted to CDP, whose conversion is catalyzed by nucleoside monophosphate kinase or myokinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the α(2,3)sialyltransferase acceptor compound, the released CMP re-enters the regenerating system to reform CDP, CTP and CMP-sialic acid. The formed PPi can be scavenged as discussed below, forming inorganic phosphate (Pi) as a byproduct or the PPi or Pi can be removed from solution via precipitation with added divalent metal cations. Pyruvate is also a byproduct.

The byproduct pyruvate can also be made use of in another reaction in which N-acetylmannosamine (ManNAc) and pyruvate are reacted in the presence of NeuAc aldolase (EC 4.1.3.3) to form sialic acid. Thus, the sialic acid can be replaced by ManNAc and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase. In addtion, ManNAc can be made by conversion of GlcNAc as described by Simon et al., *J. Am. Chem. Soc.* 110:7159 (1988). The enzymatic synthesis of sialic acid and its 9-substituted derivatives and the use of a resulting sialic acid in a different sialylating reaction scheme is disclosed in International application WO 92/16640, published on Oct. 1, 1992, and incorporated herein by reference.

As used herein, the term "pyrophosphate scavenger" refers to substances that serve to remove inorganic pyrophosphate from a reaction mixture of the present invention. Inorganic pyrophosphate (PPi) is a byproduct of the preparation of CMP-NeuAc. Produced PPi can feed back to inhibit other enzymes such that glycosylation is reduced. However, PPi can be degraded enzymatically or by physical means such as sequestration by a PPi binding substance. For instance, PPi can be removed by hydrolysis using inorganic pyrophosphatase (PPase; EC 3.6.1.1), a commercially available PPi catabolic enzyme (Sigma Chem. Co., St. Louis, Mo.; Boehringer Mannheim, Indianapolis, Ind.), and that or a similar enzyme serves as the pyrophosphate scavenger.

As explained below, the preferred method of removing PPi or Pi from the reaction mixture is to maintain divalent metal cation concentration in the medium. In particular, the cations and the inorganic phosphate produced form a complex of very low solubility. By supplementing the cations which are lost by precipitation with pyrophosphate, the rate of reaction can be maintained. As shown below, when cation concentration is maintained in an optimal range, the sialyl transferase reaction cycle can be driven to completion.

The concentrations or amounts of the various reactants used in this trans-sialylation process depend upon numerous factors including reaction conditions such as temperature and pH value, and the choice and amount of acceptor saccharides to be sialylated. Because this sialylation process permits regeneration of activating nucleotides, activated donor sialic acid and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, sialic acid and enzymes are selected such that sialylation proceeds until the acceptor is consumed.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

A reagent which is recycled throughout the process is CMP/CDP/CTP. Thus, one can begin the reaction with any single species or combination of CMP, CDP and CTP. Inasmuch as CMP is the less expensive and most readily available of that group, CMP is typically used to start the reaction, with the amounts discussed before being those for the total amount of the species or combination used.

The above ingredients are combined by admixture in an aqueous reaction medium (solution). That medium has a pH value of about 6 to about 8. The medium is devoid of chelators that bind enzyme cofactors such as $Mg^{+2}$ or $Mn^{+2}$. The selection of a medium is based on the ability of the medium to maintain pH value at the desired level. Thus, in some embodiments, the medium is buffered to a pH value of about 7.5, preferably with HEPES. If a buffer is not used, the pH of the medium should be maintained at about 6 to 8, preferably about 7.2 to 7.8, by the addition of base. A suitable base is NaOH, preferably 6M NaOH.

The reaction medium may also comprise solubilizing detergents (e.g., Triton or SDS) and organic solvents such as methanol or ethanol, if necessary. In addition, the enzymes are preferably utilized free in solution, but can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about zero degrees C to about 45° C., and more preferably at about 20° C. to about 30° C.

The reaction mixture so formed is maintained for a period of time sufficient for the acceptor to be sialylated to form a desired sialyl galactoside (sialoside) product. Some of that product can often be detected after a few hours, with recoverable amounts usually being obtained within 24 hours. It is preferred to optimize the yield of the process, and the maintenance time is usually about 36 to about 240 hours.

The produced sialyl galactoside can be used without purification. However, it is usually preferred to recover the product. Standard, well known techniques for recovery of sialylated saccharides such as thin or thick layer chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. Using such techniques, sialyl galactosides of the invention (e.g., sialyl lactose) can be produced at essentially 100% purity, as determined by proton NMR and TLC.

These compounds can then be used in a variety of applications, e.g., as antigens, diagnostic reagents, or as therapeutics. Thus, the present invention also provides pharmaceutical compositions which can be used in treating a variety of conditions. The pharmaceutical compositions are comprised of compounds which comprise a sialyl galactoside unit. Pharmaceutical compositions of the invention are suitable for use in a variety of drug delivery systems. Suitable formulations for use in the present invention are found in *Remington's Pharmaceutical Sciences,* Mace Publishing Company, Philadelphia, Pa., 17th ed. (1985). For a brief review of methods for drug delivery, see, Langer, *Science* 249:1527–1533 (1990).

The pharmaceutical compositions are intended for parenteral, intranasal, topical, oral or local administration, such as by aerosol or transdermally, for prophylactic and/or therapeutic treatment. Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the sialyl galactosides of the invention can be incorporated into liposomes formed from standard vesicle-forming lipids. A variety of methods are available for preparing liposomes, as described in, e.g., Szoka et al., *Ann. Rev. Biophys. Bioeng.* 9:467 (1980), U.S. Pat. Nos. 4, 235,871, 4,501,728 and 4,837,028. The targeting of liposomes using a variety of targeting agents (e.g., the sialyl galactosides of the invention) is well known in the art. (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized sialyl galactosides of the invention.

Targeting mechanisms generally require that the targeting agents be positioned on the surface of the liposome in such a manner that the target moieties are available for interaction with the target, for example, a cell surface receptor. The liposome is typically fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off of the vesicle surface. Alternatively, the targeting agent can be attached to a lipid molecule to form a lipid-targeting molecule conjugate which can then be incorporated into a pre-formed liposome.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient, but generally range from about 0.5 mg to about 2,000 mg of sialyl galactoside oligosaccharide per day for a 70 kg patient, with dosages of from about 5 mg to about 200 mg of the compounds per day being more commonly used.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight, but generally range from about 0.5 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the sialyl galactoside of this invention sufficient to effectively treat the patient.

The compounds may also find use as diagnostic reagents. For example, labeled compounds can be used to locate areas of inflammation or tumor metastasis in a patient suspected of having an inflammation. For this use, the compounds can be labeled with $^{125}$I, $^{14}$C, or tritium.

The sialyl galactoside of the invention can be used as an immunogen for the production of monoclonal or polyclonal antibodies specifically reactive with the compounds of the invention. The multitude of techniques available to those skilled in the art for production and manipulation of various immunoglobulin molecules can be used in the present invention. Antibodies may be produced by a variety of means well known to those of skill in the art.

The production of non-human monoclonal antibodies, e.g., murine, lagomorpha, equine, etc., is well known and may be accomplished by, for example, immunizing the animal with a preparation containing the sialyl galactoside of the invention. Antibody-producing cells obtained from the immunized animals are immortalized and screened, or screened first for the production of the desired antibody and then immortalized. For a discussion of general procedures of monoclonal antibody production see Harlow and Lane, *Antibodies, A Laboratory Manual* Cold Spring Harbor Publications, N.Y. (1988).

The following examples are offered solely for the purposes of illustration, and are intended neither to limit nor to define the invention.

EXAMPLE 1

This example illustrates the production of α-N-acetylneuraminic acid(2,3)β-galactosyl(1,4)glucose using the sialyl transferase cycle with control of the manganese ion concentration.

In a polypropylene vessel, phosphoenolpyruvate trisodium salt (285.4 g, 1.22 mol) and sialic acid (197 g, 0.637 mol) were dissolved in 5 L of water and the pH was adjusted to 7.1 with 6M NaOH. Cytidine-5'-monophosphate (5.14 g, 15.9 mmol) and potassium chloride (7.9 g, 0.106 mol) were added and the pH was re-adjusted to 7.45 with 6M NaOH. Pyruvate kinase (28,000 units), myokinase (17,000 units), adenosine triphosphate (0.98 g, 1.6 mmol), CMP NeuAc synthetase (1325 units), α2,3 sialyltransferase (663 units) and MnCl$_2$.4H$_2$O (52.4 g, 0.265 mol) were added and mixed. To a 3.7 L portion of the resulting mixture was added lactose (1 19 g, 0.348 mol) and sodium azide (1.75 g). The reaction mixture was kept at room temperature and monitored daily by thin layer chromatography (tlc) and ion chromatography. After two days, additional enzymes were added as follows: pyruvate kinase (38,100 units), myokinase (23,700 units), CMP NeuAc synthetase (935 units), and α2,3 sialyltransferase (463 units). The pH was periodically adjusted to 7.5 with 6M NaOH. Additionally, the manganese ion concentration was measured and supplemented as shown in the table below.

TABLE

| Day | [Mn$^{++}$] (measured, mM) | Loss of Mn$^{++}$ (from previous day) | Amount Supplemented (mL of 1 M, final added conc) |
|---|---|---|---|
| 1 | 28 | 22.0 | none |
| 2 | 23.9 | 4.1 | none |
| 3 | 10.7 | 13.2 | 111 mL, +30 mM |
| 4 | 1.4 | 39.3 | 111 mL, +30 mM |
| 5 | 3.0 | 28.4 | 148 mL, +40 mM |
| 6 | 12.9 | 30.1 | 74 mL, +20 mM |
| 7 | 10.0 | 22.9 | 80 mL, +20 mM |
| 8 | 12.0 | 18.0 | 80 mL, +20 mM |
| 9 | 24.3 | 7.7 | none |

On day 9, the reaction was essentially complete by tlc. As the results in the table indicate, the depletion of Mn$^{++}$ resulted in additional amounts of MnCl$_2$.4H$_2$O being added almost daily to maintain the metal ion concentration. Manganese ion is a required cofactor for at least one enzyme in the sialyl transferase cycle. However, the manganese ion and the inorganic phosphate produced (see FIG. 1) form a complex of very low solubility. Because of this limited solubility, the transferase cycle can continue to proceed, but at reduced reaction rates. By supplementing the manganese ions which are lost by precipitation with pyrophosphate, the rate of reaction can be maintained. Thus, when manganese ion concentration is maintained in an optimal range, the sialyl transferase reaction cycle can be driven to completion.

All publications, patents and patent applications mentioned in this specification are herein incorporated by reference into the specification to the same extent as if each individual publication, patent or patent application was specifically and individually indicated to be incorporated herein by reference.

The above description is illustrative and not restrictive. Many variations of the invention will become apparent to those of skill in the art upon review of this disclosure. Merely by way of example a number of substrates, enzymes, and reaction conditions can be substituted into the glycosyl transferase cycles as part of the present invention without departing from the scope of the invention. The scope of the invention should, therefore, be determined not with reference to the above description, but instead should be determined with reference to the appended claims along with their full scope of equivalents.

What is claimed is:

1. A method for sialylating a galactose-containing acceptor, comprising:
   (a) providing a reaction medium comprising:
      (i) a sialyl transferase;
      (ii) a catalytic amount of a CMP-sialic acid synthetase;
      (iii) a sialic acid;
      (iv) an acceptor for said sialyltransferase having a galactosyl unit;
      (v) a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP; and (vi) a divalent metal cation at a concentration of between about 2 mM to about 75 mM; and as a separate step occurring after initiation of a reaction in said reaction medium;

(b) adding sufficient divalent metal cation to said reaction medium to restore a portion of said divalent cation lost during the course of the reaction to thereby achieve or maintain a concentration of said divalent metal cation of between about 2 mM and about 75 mM.

2. A method in accordance with claim 1 wherein said divalent metal cation is a member selected from the group consisting of $Mn^{++}$, $Mg^{++}$, $Ca^{++}$, $Co^{++}$, $Zn^{++}$ and combinations thereof.

3. A method in accordance with claim 1 wherein said sialyltransferase is $\alpha(2,3)$sialyltransferase.

4. A method in accordance with claim 1 wherein said sialyltransferase is $\alpha(2,6)$sialyltransferase.

5. A method in accordance with claim 1 wherein said sialyltransferase is $\alpha(2,3)$sialyltransferase and said divalent metal cation is $Mn^{++}$.

6. A method in accordance with claim 1 wherein said sialic acid is 5-N-acetylneuraminic acid.

7. A method in accordance with claim 1 wherein said acceptor is lactose.

8. A method in accordance with claim 1 wherein said sialic acid is 5-N-acetylneuraminic acid and said acceptor is lactose.

9. A method in accordance with claim 1, wherein said sialic acid is 5-N-acetylneuraminic acid, said acceptor is lactose, said nucleoside triphosphate is ATP, said phosphate donor is phosphoenolpyruvate, said kinase is pyruvate kinase, said nucleoside monophosphate kinase is myokinase, said divalent metal cation is $Mn^{++}$ and said sialyltransferase is $\alpha(2,3)$sialyltransferase.

10. A method in accordance with claim 1, wherein said sialic acid is 5-N-acetylneuraminic acid, said acceptor is lactose, said nucleoside triphosphate is ATP, said phosphate donor is acetyl phosphate, said kinase is acetyl kinase, said nucleoside monophosphate kinase is myokinase, said divalent metal cation is $Mn^{++}$ and said sialyltransferase is $\alpha(2,3)$sialyltransferase.

11. A method in accordance with claim 1, wherein said reaction cycle is conducted in a buffered aqueous medium having a pH value of about 6 to about 8.

12. A method for the enzymatic formation of sialyl$\alpha2\rightarrow3\beta$galactoside, comprising:

(a) combining the following components in a single vessel to form a reaction mixture:
(i) a catalytic amount of an $\alpha(2,3)$sialyltransferase;
(ii) a catalytic amount of a CMP-sialic acid synthetase;
(iii) a sialic acid;
(iv) an acceptor for said $\alpha(2,3)$sialyltransferase having a galactosyl unit;

(v) a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP; and (vi) a reaction medium containing a divalent metal cation in an amount of from about 2 mM to about 75 mM and having a pH value of about 6 to about 8; and as separate steps occurring after initiation of a reaction in said medium (b) maintaining said reaction medium at a temperature of about 0° C. to about 45° C. and adding sufficient divalent metal cation to said reaction medium to restore a portion of said divalent cation lost during the course of the reaction to thereby achieve or maintain a concentration of said divalent metal ion of between about 2 mM and about 75 mM for a time period sufficient for said acceptor (iv) to be sialylated and form said sialyl$\alpha2\rightarrow3\beta$galactoside.

13. A method in accordance with claim 12, wherein said divalent metal cation is a member selected from the group consisting of $Mn^{++}$, $Mg^{++}$, $Ca^{++}$, $Co^{++}$, $Zn^{++}$ and combinations thereof.

14. A method in accordance with claim 12, wherein said divalent metal cation is $Mn^{++}$.

15. A method in accordance with claim 12, wherein said sialic acid is 5-N-acetylneuraminic acid.

16. A method in accordance with claim 12, wherein said acceptor is lactose.

17. A method in accordance with claim 12, wherein said sialic acid is 5-N-acetylneuraminic acid and said acceptor is lactose.

18. A method in accordance with claim 12, further comprising recovering said formed sialyl$\alpha2\rightarrow3\beta$galactoside.

19. A method in accordance with claim 12, wherein said sialic acid is 5-N-acetylneuraminic acid, said acceptor is lactose, said nucleoside triphosphate is ATP, said phosphate donor is phosphoenolpyruvate, said kinase is pyruvate kinase, said nucleoside monophosphate kinase is myokinase and said divalent metal cation is $Mn^{++}$.

20. A method in accordance with claim 12, wherein said sialic acid is 5-N-acetylneuraminic acid, said acceptor is lactose, said nucleoside triphosphate is ATP, said phosphate donor is acetyl phosphate, said kinase is acetyl kinase, said nucleoside monophosphate kinase is myokinase and said divalent metal cation is $Mn^{++}$.

* * * * *